United States Patent [19]

Brader

[11] Patent Number: 4,869,718
[45] Date of Patent: Sep. 26, 1989

[54] TRANSCRICOTHYROID CATHETERIZATION DEVICE

[76] Inventor: Eric W. Brader, 42 Canter Dr., Sewickley, Pa. 15143

[21] Appl. No.: 177,585

[22] Filed: Apr. 4, 1988

[51] Int. Cl.$^4$ .................. A61M 16/00; A61M 5/00
[52] U.S. Cl. .................................. 604/164; 604/179; 128/207.17
[58] Field of Search ............... 604/177, 174, 179, 164, 604/165; 128/207.14–207.17, DIG. 26

[56] References Cited

U.S. PATENT DOCUMENTS

| | | | |
|---|---|---|---|
| 4,292,970 | 10/1981 | Hession, Jr. | 604/164 X |
| 4,488,545 | 12/1984 | Shen | 128/204.25 |
| 4,520,813 | 6/1985 | Young | 128/207.17 |
| 4,686,977 | 8/1987 | Cosma | 128/207.17 |

*Primary Examiner*—Stephen C. Pellegrino
*Attorney, Agent, or Firm*—Webb, Burden, Ziesenheim & Webb

[57] ABSTRACT

A self-adjusting transcricothyroid catheter comprises a catheter attached near its proximal end to a fastener plate. The attachment means permits rotation/translation of the catheter relative to the fastener plate, rendering the catheter self-adjusting to movement of the neck. The fastener plate is adapted for topical placement adjacent the site of cricothyroid puncture and is held in place by attached strap means which encircle the neck and which optionally form a part of a cervical immobilization device. The minimized length of the catheter minimizes or eliminates kinking and/or knotting of the catheter during its insertion, and the ability of the catheter to self-adjust to movement minimizes trauma and bleeding during use.

14 Claims, 2 Drawing Sheets

TRANSCRICOTHYROID CATHETERIZATION DEVICE

FIELD OF THE INVENTION

The present invention relates to a transcricothyroid catheter adapted for use with high frequency jet ventilation.

INTRODUCTION

Respiratory ventilation augmentation systems have typically delivered air and/or oxygen to the patient's lungs via either endotracheal or tracheostomy tubes. Ordinarily, these systems have incorporated air compressors which deliver air in a volume and pattern which approximates normal breathing.

High Frequency Jet Ventilation (HFJV) systems, in contrast with these conventional systems, deliver higher velocity air in higher frequency than do the prior art devices. As a result, only a narrow tube need be inserted into the trachea of a patient ventilated with HFJV, the lungs being protected from aspiration by pneumatic valving. With HFJV, moreover, the lungs need not expand and contract to the usual extent: HFJV air pulses themselves promote air circulation and gas exchange in the lungs. HFJV accordingly neither forces lung expansion and contraction nor interferes with spontaneous breathing.

BACKGROUND OF THE INVENTION

High Frequency Jet Ventilation is most commonly administered via transcricothyroid puncture, or transtracheal puncture, with placement of a narrow catheter. A number of transcricothyroid or transtracheal puncture/catheter placement devices are known in the art. For example, U.S. Pat. No. 4,488,545 to Shen discloses a catheter placement device for use in introducing high frequency jet ventilation gas to the trachea of a patient. The catheter introducer of the catheter placement device contains a spring-actuated retractable needle, and the catheter introducer is designed to be removed from the catheter prior to HFJV connection. U.S. Pat. No. 4,593,687 to Gray et al. discloses a tracheal catheter tube having a removable magnetic stylet, which stylet upon removal from the inserted catheter permits expansion of the bulbed end to lock the tube inside the tracheal wall. U.S. Pat. No. 4,364,391 discloses a tracheostomy apparatus which includes structural elements used in sequence. Two coaxial needles are inserted into the tracheal lumen. After removal of the inner needle, a catheter is placed by inserting the leader of a dilator contained within the catheter through the outer needle, removing the outer needle, pushing the catheter into place and removing the dilator. U.S. Pat. No. 3,788,326 to Jacobs discloses a distally perforated ventilation catheter which can be introduced either through the mouth or percutaneously. U.S. Pat. No. 4,556,059 to Adamson, Jr., discloses a spring-operated tracheotome.

Theoretically, percutaneous catheters for tracheal insertion should be easy to position and should lead to minimal bleeding and/or complications due to their relatively narrow diameter. In practice, however, particularly in the emergency setting, placement of prior art, relatively large diameter percutaneous tracheostomy catheters is difficult, must be performed slowly, and has resulted in unacceptable blood loss and trauma. Even under conditions of cervical vertebrae immobilization, as is customary in emergency care generally, blood loss and trauma (and resultant complications) occur as a result of inevitable anatomic movements in the densely vascularized neck area. Accordingly, during swallowing, breathing (if spontaneous breathing is present) and musculature movement, bleeding is exacerbated, catheter anchors tend to dislodge and the catheters themselves tend to knot or kink. In the event of any of these undesired occurrences, adjustment or reinsertion of the catheter becomes necessary, and the adjustment or reinsertion itself inevitably produces more trauma (including loss of ventilatory support and airway control) and/or bleeding.

In view of the above, a need persists for a transcricothyroid catheter which minimizes or eliminates knotting or kinking, bleeding, neck trauma and resultant complications. Such a device would optimally self-adjust to accommodate normal anatomic movement of the neck without dislodging or compressing surrounding tissues, to enable the catheter to remain in place for extended periods.

SUMMARY OF THE INVENTION

In order to meet this need, the present invention is a self-adjusting transcricothyroid catheter wherein the catheter is attached near its proximal end to a fastener plate by means of a rotatable joint. The fastener plate is adapted for topical placement adjacent the site of cricothyroid puncture and is held in place by attached strap means which encircle the neck and which optionally form a part of a cervical immobilization device. The rotatable joint connecting the catheter and the fastener plate permits the catheter to self-adjust to normal anatomic movement of the neck. The minimized length of the catheter minimizes knotting or kinking of the catheter after its insertion. The transcricothyroid catheter may be straight or curved and is accompanied by a corresponding needle and a corresponding obturator, each of which when axially disposed within the catheter extends at least one millimeter beyond the distal end of the distal cannula. Insertion is accomplished by inserting the needle within the catheter and using the needle/catheter combination to perform a cricothyroid puncture to and into the trachea of a patient. The needle is then removed, is replaced by the obturator and the catheter is advanced into its final position. The dilator-stent, proximal portion of the catheter, spreads the cricothyroid membrane without further puncture or incision. Upon removal of the obturator, the catheter may be connected with an HFJV system for use. The system is suitable for use in both emergency and general hospital treatment of respiratory insufficiency.

DETAILED DESCRIPTION OF THE INVENTION

Figure 1:
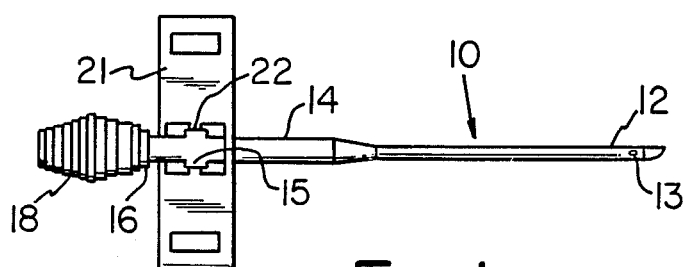
FIGS. 1 and 2 illustrate plan views of a first embodiment of the transcricothyroid catheter of the present invention, shown with and without the axially disposed corresponding needle, respectively.
Figure 2:
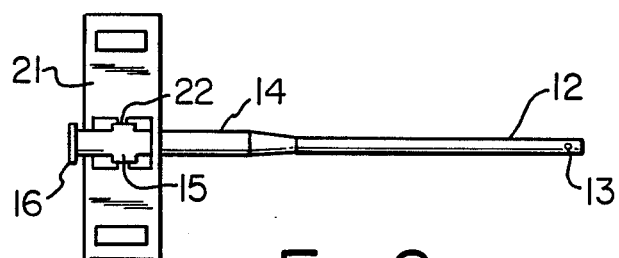
Figure 3:
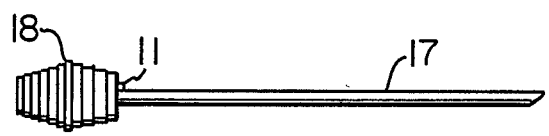
FIG. 3 is a plan view of a needle adapted for coaxial insertion within the transcricothyroid catheter of FIG. 2.

A first embodiment of the invention is illustrated in FIGS. 1-5. Referring now to FIG. 2, the transcricothyroid catheter 10 is illustrated showing its two major structural sections, the hollow tube comprising the distal cannula 12 and the proximal cannula 14, and the fastener plate 21 having two strap-receiving apertures therein. The distal and proximal cannulas 12, 14 are colinear. The distal cannula 12 contains two additional apertures 13 near the distal terminus as shown, one on each side. The additional apertures 13 permit air flow should the main outlet of the distal cannula become obstructed during use, and also prevents aspiration during initiation of ventilation secondary to the venturi effect.

As shown in FIGS. 1 and 2, the proximal cannula 14 is rotatably mounted on the fastener plate 21 by means of the proximal cannula connector 15. The proximal cannula connector 15 is an intersecting channel structure located approximately one quarter of the length of the proximal cannula 14 away from its proximal terminus. More particularly, the short channel which constitutes the proximal cannula connector 15 is a hollow tube segment which intersects the proximal cannula 14 at a 90 degree angle. The proximal cannula connector 15 may be further viewed in FIG. 5; each of the two ends of the structure is open to the ambient air. The proximal cannula connector 15 is thus adapted cooperatively to attach to the fastener plate 21, as described below.

Figure 5:
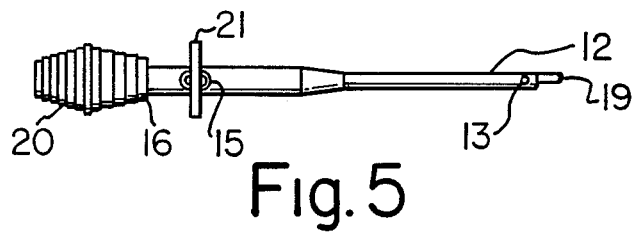
FIG. 5 is a side elevational view of the first embodiment of the transcricothyroid catheter.
Figure 7:
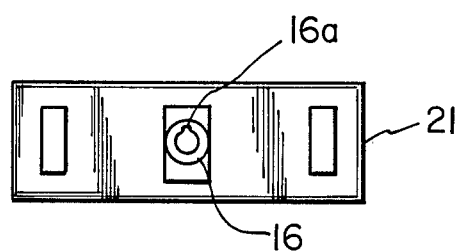
FIG. 7 is an end elevational view of the first embodiment of the transcricothyroid catheter.

The fastener plate 21 having two strap-receiving apertures therein is illustrated in FIGS. 1, 2, and 7. The fastener plate is a flat structure having both a generally rectangular shape and also having a cutout configuration as shown in FIGS. 1, 2, and 7. The thickness of fastener plate 21 is shown in FIG. 5. (FIG. 5, a side elevational view, shows the fastener plate 21 rotated 90 degrees from its position as shown in FIGS. 1 and 2.) The fastener plate shaft 22 is shown in FIGS. 1 and 2 extending through the proximal cannula connector; both the width and height of the fastener plate shaft 22 are less than the inside diameter of the proximal cannula connector 15. As may be visualized from the Figures, therefore, the proximal cannula connector 15 may rotate in three dimensions. First, the proximal cannula 14 may rotate freely about the fastener plate shaft 22 as its axle. Additionally, however, due to the space between the inside surfaces of the proximal cannula connector 15 and the fastener plate shaft 22, the proximal cannula 14 may also rotate somewhat in the second and third dimensions. That is, due to the space between all sides of the fastener plate shaft 22 and the surrounding proximal cannula connector 15, the proximal cannula 14 can rock back and forth in two dimensions as well as rotate freely in a third. The overall configuration of the proximal cannula 15 and the fastener plate shaft 22 therefore provides "universal joint" function of a specialized nature. In addition, the proximal cannula connector 15 can slide freely, or "translate," along the length of the fastener plate shaft 22, as stress is applied to it. This rotational and/or translational mobility of the proximal cannula makes the cannula self-adjusting, as is described further below.

The proximal terminus of the proximal cannula has a proximal cannula rim 16 thereon. The proximal cannula rim 16 provides an inlet for HFJV, which can be connected by means known in the art. The proximal cannula rim 16 has a key notch 16a therein, shown in FIG. 7. Through this proximal cannula rim 16 may be inserted either the needle 17 of FIG. 3, having the needle grip 18, or the obturator 19 of FIG. 4, having the obturator grip 20. For alignment purposes and for prevention of unwanted rotation, either the needle grip key 11 or the obturator grip key 13 may be press fit into the key notch 16a when either the needle 17 or obturator 19 is fully inserted into the transcricothyroid catheter 10.

The dimensions of the first embodiment of the transcricothyroid catheter 10 shown in FIGS. 1-5 are outlined below. The needle 17 of FIG. 3 has a shaft approximately 7 centimeters in length and the needle grip 18 approximately 1.5 centimeters in length. The diameter of the needle is approximately 1.7 millimeters. The dimensions of the obturator 19 and the obturator grip 20 are identical to the dimensions of the needle 17 and the needle grip 18; the obturator, of course, does not have the pointed tip as does the needle 17. The transcricothyroid catheter 10 from its proximal cannula rim 16 to its distal tip of the distal cannula 12 is approximately 6.8 centimeters, so that the needle 17 and the obturator 19 extend 2-4 millimeters beyond the distal terminus of the distal cannula 12 when the needle 17 or obturator 19 is in position. The distal cannula 12 has an outside diameter of approximately 2.0 millimeters and an inside diameter of approximately 1.8 millimeters; the proximal cannula 14 has an outside diameter of approximately 3.5 millimeters and an inside diameter of about 3.0 millimeters. Alternatively, the inside diameter of the proximal cannula 14 may be between 1.8-3.0 millimeters, with a sharp or gradual taper, so long as the inside diameter at the point nearest the proximal cannula rim 16 is the 3.0 millimeters standard in the art. Also, outside diameters of the proximal and distal cannulas 14, 12 may be decreased so long as adequately strong materials which do not kink are used. The fastener plate 21 is approximately 4 centimeters in length and bears the apertures as illustrated in FIGS. 1 and 2. The thickness of the fastener plate 21 is on the order of 1-2 millimeters. Of course, overall dimensions for the combined structures may vary even though the general proportions should remain approximately the same. However, the taper between the proximal and distal cannulas 14, 12 of FIGS. 1, 2 and 5 may be over a greater length than that shown without affecting the present invention.

Insertion and use of the first embodiment of the transcricothyroid catheter 10 is accomplished as follows. The needle 17 is inserted and axially disposed within the transcricothyroid catheter 10 of FIG. 2 to yield the combination as shown in FIG. 1. The pointed tip of the needle 17 extends beyond the distal terminus of the distal cannula 12 when the needle grip 18 is positioned immediately adjacent the proximal cannula rim 16. The combination as shown in FIG. 1 is used by the physician or health care provider to perform a cricothyroid puncture, with preliminary incision with a small lancet, if desired, and the needle/cannula combination is inserted through the tissue of the neck until the tip of the needle 17 is inside the tracheal wall. In other words, cricothyroid puncture and insertion of the distal cannula is performed with the needle 17 in place until approximately 3-4 centimeters of the distal cannula 12 has passed through the skin and into position within the lumen. The needle grip 18 is then grasped and the needle 17 is withdrawn from the transcricothyroid catheter 10.

Figure 4:
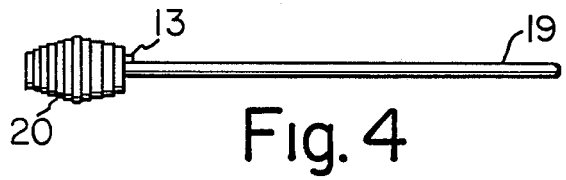
FIG. 4 is a plan view of a corresponding obturator adapted for coaxial insertion within the transcricothyroid catheter of FIG. 2.

After removal of the needle 17, the obturator 19 having the obturator grip 20 of FIG. 4 is inserted and axially disposed within the transcricothyroid catheter 10 of FIG. 2. The combination is then inserted another 1-7 centimeters, and the rounded blunt tip of the obturator 19 prevents any puncturing of the tracheal wall.

Figure 6:
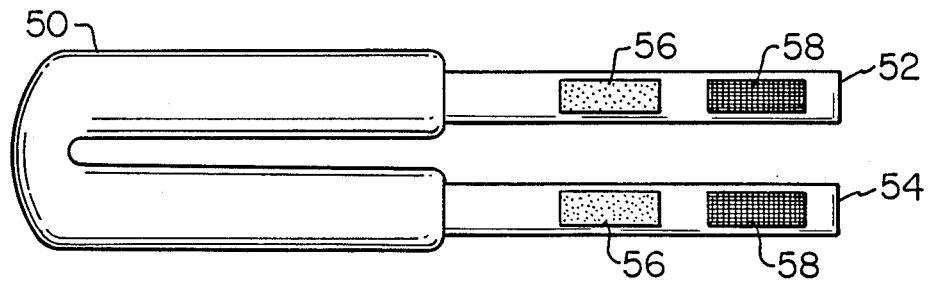
FIG. 6 is a plan view of strap means adapted to encircle the neck and to attach to position the transcricothyroid catheter.

After the transcricothyroid catheter 10 has been inserted, the fastener plate 21 having two strap-receiving apertures therein is anchored in place on the neck by means of neck-encircling straps. An example of neck-encircling straps is shown in FIG. 6, in which a neck-encircling cuff 50 has first and second fastener-plate engaging straps 52, 54 thereon, each of which respectively bears first and second cooperative fastening patches 56, 58. (The cooperative fastening patches 56, 58 will ordinarily be constructed of loop-and-latch material such as is sold under the trade name VELCRO ®.) As shown in FIG. 6, the neck-encircling cuff 50 is not a cervical support but is a neck-encircling means as illustrated. The first and second fastener-plate engaging straps 52, 54 thread through the fastener plate 21 to fix the position of the fastener plate 21 to the neck of the patient. This arrangement of the fastener plate 21 adjacent the transcricothyroid catheter 10 and flush against the patient's skin, accommodates a wide variety of insertion angles of the transcricothyroid catheter 10. This aspect of the present invention is essential inasmuch as precise control of insertion angle under emergency conditions is difficult to impossible. As an additional feature, once the fastener plate 21 is in place, it does not impede rotational and/or translational self-adjustment of the proximal cannula 14 in response to normal anatomic movement of the neck, as a result of the rotation and/or translation permitted by the proximal cannula connector 15 and its cooperating fastener plate shaft 22.

In the embodiment of the invention illustrated in FIGS. 1-5 and 7, the generally annular space between the proximal cannula connector 15 and the fastener plate shaft 22 enables slight communication between the ambient air and the passage through the distal and proximal cannulas 12, 14. As a practical matter, the self-adjustment advantage which this space affords outweighs the minor disadvantage caused by leakage of air in and out of the proximal cannula connector 15. In practice, this slight air loss has not proved in any way serious. If desired, however, a resilient, air-impermeable sealant material may be provided at each end of the proximal cannula connector 15 to provide a seal between the proximal cannula connector 15 and the fastener plate shaft 22. Such a gasket or membrane, when fabricated from a resilient elastomer, does not impede the rotational and/or translational self-adjustment of the proximal cannula connector 15 relative to the fastener plate 21. The gasket or membrane as described is optional and does not appear in any of the illustrations in FIGS. 1-5 or 7.

Figure 8:
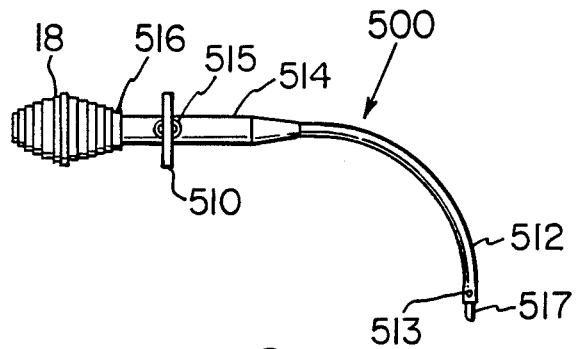
FIGS. 8 and 9 illustrate side views of a second embodiment of the transcricothyroid catheter, shown with and without the axially disposed corresponding needle, respectively.
Figure 9:
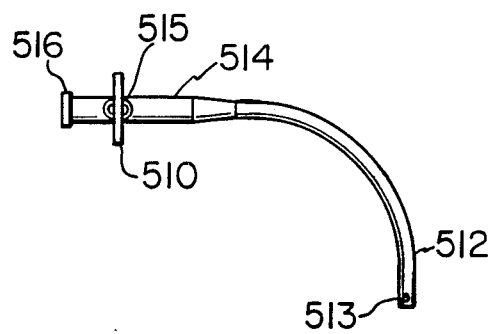
Figure 10:
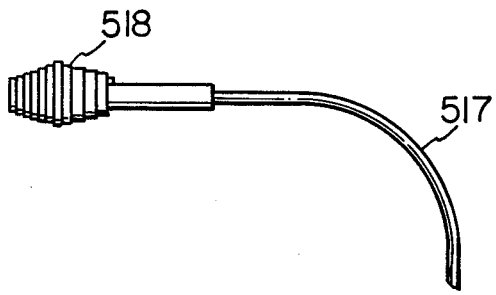
FIGS. 10 and 11 illustrate in side elevational view, respectively, the curved needle and curved obturator adapted for use with the third curved embodiment of FIGS. 8 and 9.
Figure 11:
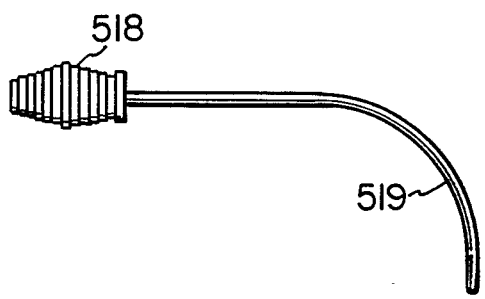

Referring now to FIGS. 8-11, the transcricothyroid catheter 500 as shown in FIGS. 8 and 9 represents a second embodiment of the invention. The second embodiment is nearly identical to the first embodiment illustrated in FIGS. 1-5 and 7 except that the proximal and distal cannulas 514, 512 and the corresponding needle 517 are permanently curved as shown. The curved needle 517 and the curved obturator 519 are separately illustrated in FIGS. 10-11. More particularly, the transcricothyroid catheter 500 of FIGS. 8 and 9 include a distal curved cannula 512, an additional aperture 513, a proximal curved cannula 514 and a proximal cannula connector 515. The proximal curved cannula 514 terminates in a proximal cannula rim 516 having a key notch (not shown). The proximal cannula connector 515 mounts in the fastener plate 510 by means of a fastener plate shaft (not shown) identical to the fastener plate shafts of the first two embodiments of the invention. The cooperating curved needle 517 and curved obturator 519 have grips 518 and 520, respectively. The use, structure (including dimensions) and operation of the third embodiment of the invention is identical to that of the first and second embodiments except that the curved configuration of not only the combined cannulas 514, 512 but also the needle 517 and obturator 519 facilitate cricothyroid puncture and ultimate placement of the transcricothyroid catheter 500 in the trachea.

Selection of materials for the fabrication of the various transcricothyroid catheter devices discussed herein is not critical, but the following materials are exemplary. The needle shafts are ordinarily constructed of stainless steel or titanium alloys, and the respective needle grips may be the same material or a polymer material such as polyurethane, polyacrylate, polyethylene, polypropylene or the like. The obturator may be fabricated from materials which are at least substantially rigid, including but not limited to stainless steel, titanium alloys, polyacrylate, high density polyethylene, and the like. The fastener plates as described may be manufactured of any of the above materials and may also include elastomers including the medical grade silicone rubber (polyorganosiloxane) resins known in the medical art. The proximal and distal cannulas including the cannula connector may be manufactured of materials known in the art, such as polypropylene, flexible polyethylene, polyurethane, polyacrylate, polycarbonate, or polyorganosiloxane.

The neck-encircling means as illustrated in FIG. 5 is susceptible of wide variation without departure from the spirit of the invention. The neck-encircling means may be virtually any strap, cuff, or cervical collar device which is adapted with straps which can interconnect with the fastener plate of the transcricothyroid catheter in the area of the cricothyroid puncture.

Additional changes and modifications may be made to the embodiments described with particularity herein without departing from the nature of the present invention. For example, more than two apertures may be provided near the distal terminus of the distal cannula to ensure air passage should the main cannula outlet become obstructed. Likewise, inasmuch as universal joint technology is well known in the connection of rotatable structures, the proximal cannula connector as illustrated in the figures may be adapted to include alternate known "universal joints". Preferably, the universal joint selected will be adapted to allow for lateral translation of the proximal cannula relative to the fastener plate. For this reason, the fastener plate need not be an actual plate, but may comprise a fastener structure having means for securing at least one neck-encircling strap and means for engaging the proximal cannula connector. Although the present invention includes as critical the self-adjusting capability between the proximal cannula and the fastener plate, therefore, the self-adjusting rotation between the proximal cannula and the fastener plate may be accomplished by other rotatable/translatable joints in addition to the proximal cannula connectors as illustrated. One additional specific example of this includes the arrangement wherein short pins extend from either side of the catheter and mount within a block, said block being attached to the neck-encircling strap and having appropriate pin-receiving apertures therein.

Other variations and modifications may be made to the present invention, and the invention is therefore to be limited only insofar as is set forth in the accompanying claims.

I claim:

1. A self-adjusting transcricothyroid catheter, comprising:
    a hollow tube comprising a proximal cannula and a distal cannula, said proximal cannula further comprising a dilator-stent adapted to spread the cricothyroid without further puncture or incision;
    a proximal cannula connector affixed to said proximal cannula; and
    a fastener structure having means for securing at least one neck-encircling strap and further having means for engaging said proximal cannula connector, whereby, when said fastener structure and said proximal cannula connector are engaged, said proximal and distal cannulas may rotate relative to said fastener structure to provide for self-adjustment of the positioned transcricothyroid catheter.

2. The transcricothyroid catheter according to claim 1, wherein said fastener structure is a fastener plate.

3. The transcricothyroid catheter according to claim 2, wherein said fastener plate has two strap-receiving apertures therein.

4. The transcricothyroid catheter according to claim 1, wherein said proximal cannula connector is integrally formed with said proximal cannula.

5. The transcricothyroid catheter according to claim 4, wherein said proximal cannula connector is a hollow tube segment which intersects said proximal cannula at an approximate 90 degree angle.

6. The transcricothyroid catheter according to claim 5, wherein said fastener means is a fastener plate having two strap-receiving apertures therein and further having a fastener plate shaft thereon adapted for engaging said proximal cannula connector.

7. The transcricothyroid catheter according to claim 6, wherein said fastener plate shaft and said proximal cannula connector are separated by a generally annular space.

8. The transcricothyroid catheter according to claim 4 wherein said proximal cannula connector has a proximal cannula rim having a key notch therein.

9. The transcricothyroid catheter according to claim 8, wherein said proximal cannula has an outer diameter greater than the outer diameter of said distal cannula.

10. The transcricothyroid catheter according to claim 9, wherein said hollow tube is curved.

11. The transcricothyroid catheter according to claims 1 or 10, wherein a needle is axially disposed within said hollow tube and the tip of said needle extends beyond said distal cannula.

12. The transcricothyroid catheter according to claims 1 or 10, wherein a stent is axially disposed within said hollow tube and the tip of said stent extends beyond said distal cannula.

13. The transcricothyroid catheter according to claim 1, wherein said fastener structure, when in position on a wearer, is secured to two neck-encircling straps.

14. The transcricothyroid catheter according to claim 13, wherein each of said straps appends a cuff and further wherein each of said straps bears cooperative fastening patches thereon.

* * * * *